United States Patent [19]

Harman et al.

[11] Patent Number: 5,433,947
[45] Date of Patent: * Jul. 18, 1995

[54] ANTIFUNGAL SYNERGISTIC COMBINATION OF ENZYME FUNGICIDE AND NON-ENZYMATIC FUNGICIDE AND USE THEREOF

[75] Inventors: Gary E. Harman; Matteo Lorito, both of Geneva, N.Y.; Antonio D. Pietro, Cordoba, Spain; Christopher K. Hayes, Geneva, N.Y.

[73] Assignee: Cornell Research Foundation, Inc., Ithaca, N.Y.

[*] Notice: The portion of the term of this patent subsequent to Jul. 5, 2011 has been disclaimed.

[21] Appl. No.: 249,927

[22] Filed: May 26, 1994

Related U.S. Application Data

[63] Continuation of Ser. No. 990,609, Dec. 15, 1992, Pat. No. 5,326,561.

[51] Int. Cl.$^6$ .......................... A61K 37/54; C12N 9/24; C12N 9/42; A01N 43/50
[52] U.S. Cl. .............................. 424/94.61; 435/200; 435/209; 514/396; 514/423
[58] Field of Search ............... 424/94.61; 435/200, 435/209; 514/396, 423

[56] References Cited

U.S. PATENT DOCUMENTS

| | | | |
|---|---|---|---|
| 4,477,433 | 10/1984 | Hultman | 435/254 |
| 4,489,161 | 12/1984 | Papavizas | 435/254 |
| 4,751,081 | 6/1988 | Suslow et al. | 424/93 |
| 4,940,840 | 7/1990 | Suslow et al. | 435/172.3 |
| 5,173,419 | 12/1992 | Harman et al. | 435/209 |
| 5,326,561 | 7/1994 | Harman et al. | 424/94.61 |

OTHER PUBLICATIONS

Davies, D. A. L., Nature, vol. 273, 235–236 (May 18, 1978).
Harman, G. E., et al, Proceedings of EFPP/IOBC Workshop, Copenhagen, Denmark, Jul. 1991, 8 pages.
Jones, R. W., et al, Journal of General Microbiology, 134, 2067–2075 (1988).
Klemsdal, S. S., et al, 11th Nordic Postgraduate School in Plant Pathology, abstract of poster presented Feb. 3, 1992 in Tisvildeleije, Denmark.
Lorito, M., et al, Phytopathology, 82, No. 2, 245–246 (Feb. 1992).
Poulose, A. J., in Koeller, W., ed., Target Sites of Fungicide Action, CRC Press, Boca Raton, Fla, 1992, at pp. 313, 314, 317.
Roberts, D. P., et al, Phytopathology, vol. 80, No. 5, 461–465.
Richer, D. L., Pestic. Sci. 19:309–315 (1987).
Tronsmo, A., Phytopathology 79(10), 1153 (1989), entry #143.
Tronsmo, A., Norwegian Journal of Agricultural Sciences 3:157–161 (1989).
Tronsmo, A., Biological Control 1, 59–62 (1991).
Vessey, J. C., et al, Trans. Br. Mycol. Soc. 60:710–713 (1973).
The Merck Index, 10th edition, p. 244 (1983).
Jawetz, E., et al, Review of Medical Microbiology, 16th edition, p. 147 (1984).
Berkeley, R. C. W., et al, Microbiol. Polysaccharides and Polysaccharases, 285–311, 436–447 (1979).
Ordentlich, A., et al, Crop Protection, vol. 9, 363–366 (Oct. 1990).

Primary Examiner—Marion C. Knode
Assistant Examiner—Maria Luisa Osoteo

[57] ABSTRACT

Antifungal composition comprising synergistic combination of fungal cell wall degrading enzyme selected from the , group consisting of chitinolytic enzymes, glucanolytic enzymes and cellulases and non-enzymatic fungicides selected from the group consisting of sterol synthesis inhibiting fungicides (e.g., flusilazole and miconazole) and thiol group inactivating fungicides which are not specific to fungal cell membranes (e.g., captan) are applied in an antifungal effective amount to fungus to be inhibited or to a locus to be protected from said fungus.

14 Claims, 3 Drawing Sheets

ANTIFUNGAL SYNERGISTIC COMBINATION OF ENZYME FUNGICIDE AND NON-ENZYMATIC FUNGICIDE AND USE THEREOF

This invention was made at least in part with Government support under U.S.-Israel Binational Agricultural Research and Development Fund (BARD) grant number US-1723-89. The Government has certain rights in the invention.

This application is a continuation of U.S. Ser. No. 07/990,609 filed Dec. 15, 1992, now U.S. Pat. No. 5,326,561.

TECHNICAL FIELD

This invention is directed at antifungal synergistic combinations of fungal cell wall degrading enzyme and non-enzymatic fungicide and use thereof for topical or internal application in agriculture or medicine to inhibit germination or replication of fungi.

BACKGROUND OF THE INVENTION

The primary methods of controlling disease-causing fungi on crop plants and on animals, including humans, comprise treatment with synthetic chemical pesticides. However, the exposure of man and habitats to increasing amounts of pesticides has come under criticism, resulting in a search for environmentally safer methods including the use of synergistic combinations of fungicides to reduce the amounts of application.

Poulose, A. J., in Koeller, W., ed., Target Sites of Fungicide Action, CRC Press, Boca Raton, Florida, 1992, at pages 313-314 reviews the disclosures of a number of authors directed to synergistic interaction of different lytic enzymes produced by a variety of microorganisms with a small number of antifungal compounds including amphotericin B, benomyl, polyoxin B, kitazin P and nikkomycin.

SUMMARY OF THE INVENTION

It is an object of this invention to expand the range of synergistic combinations of fungicide/enzyme.

The antifungal composition of the invention herein comprises:
(a) fungal cell wall degrading enzyme, and
(b) non-enzymatic fungicide selected from the group consisting of (i) sterol synthesis inhibiting fungicides and (ii) thiol group inactivating fungicides which are not specific to fungal cell membranes,
these being present in a weight ratio of (a) to (b) ranging from 2:1 to 500,000:1 on a biologically pure enzyme basis (i.e., considering that the enzyme (a) is biologically pure),
the combination of (a) and (b) being present in an antifungal effective amount.

The fungal cell wall degrading enzyme is preferably biologically pure.

The method of the invention herein is directed to inhibiting the replication, germination or growth of a fungus and comprises contacting such fungus or the locus to be protected from such fungus with an antifungal effective amount of composition of the invention herein.

The term "fungal cell wall degrading enzyme" is used herein to mean enzyme that effects lysis of fungal cell walls.

The term "sterol synthesis inhibiting fungicides" refers to a recognized class of fungicides which inhibit a demethylation step in the synthesis of sterols specific to fungi.

The term "thiol group inactivating fungicides" is used herein to mean fungicides which inactivate coenzyme A or other thiol compounds.

The term "which are not specific to fungal cell wall membranes" excludes thiol inactivating fungicides whose primary mode of action involves binding to thiol groups located on cell membranes, such as gliotoxin.

The term "biologically pure" is used herein to mean purified to be free of contaminating protein, i.e., purified to homogeneity, based on electrophoretic analysis. The term "on a biologically pure enzyme basis" is used herein to mean considering that the enzyme is biologically pure (even if it is not).

The term "inhibit" is used herein to mean reduce the growth and/or development of fungi compared to where inhibiting agent is not present.

The term "locus to be protected from such fungus" includes seeds, roots, stems, leaves, flowers and fruits to be protected and to the soil surrounding seeds and roots to be protected, as well as animal or human tissues or organs to be protected.

DETAILED DESCRIPTION

Figure 1:
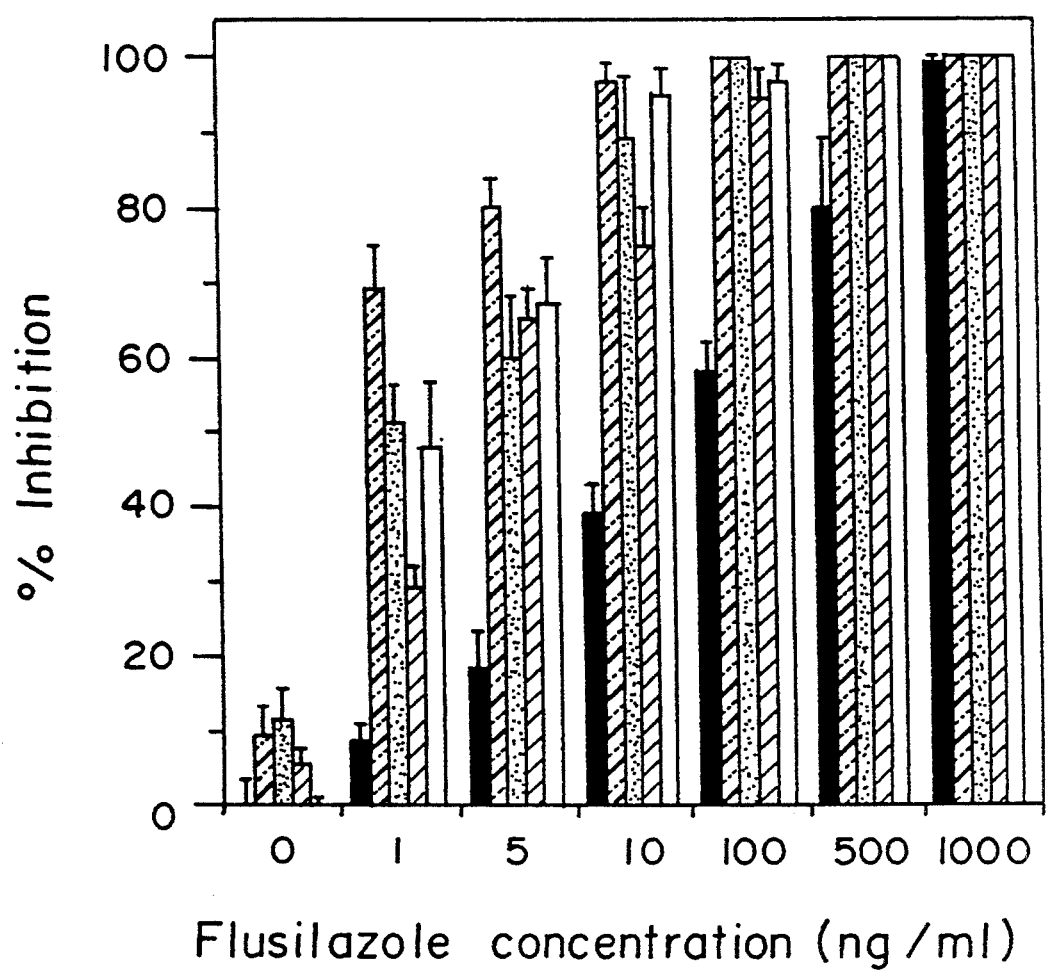
FIG. 1 is a set of bar graphs depicting % inhibition at various flusilazole concentrations, in the presence of different enzymes and in the absence of enzyme, showing results of Example II.

The fungal cell wall degrading enzymes for the composition and method herein include, for example, chitinolytic enzymes and $\beta$-1,3glucanolytic enzymes for degrading cell walls of fungi where the cell walls contain, as a major structural component, chitin and $\beta$-1,3-glucans, and cellulases for degrading cell walls of lower fungi (Oomycetes) where the cell walls contain, as a major structural component, cellulosic polysaccharides.

These enzymes are found in fungi, bacteria and higher plants. They can be used in natural form, i.e., not separated from the source, e.g., by utilizing source microorganisms in the composition herein, or they may be used in partially purified form, i.e, purified compared to natural form but with other protein present. As indicated above, the enzyme component of the composition herein is preferably used in biologically pure form. Fungal cell wall degrading enzymes are readily obtained in biologically pure form from source microorganisms by culturing the source microorganism, concentrating the culture filtrate, fractionating by gel filtration chromatography, concentrating and further purifying by chromatofocusing followed, if necessary, by isoelectrofocusing in a Rotofor cell (BioRad, Richmond, Calif.).

The chitinolytic enzymes cleave chitin, and include, for example, endochitinases, chitin 1,4-$\beta$-chitobiosidases and $\beta$-N-acetylglucosaminidases. These can be obtained from fungi, for example, from the genera *Trichoderma, Gliocladium, Lycoperdon* and *Calvatia;* from bacteria, from the genera *Streptomyces, Vibrio, Serratia* and *Bacillus;* and from higher plants, e.g., *Nicotiana, Cucumis* and *Phaesolus*.

The endochitinases are enzymes that randomly cleave chitin. Endochitinase activity is readily measured by determining optical density at 510 nm as reduction of turbidity of a 1% suspension of moist purified colloidal chitin in 100 mM sodium acetate buffer, pH 5.5, or in 50 mM KHPO$_4$ buffer, pH 6.7, after 24 hours of incubation at 30° C. For calculation of specific activity, one unit is defined as the amount of enzyme required to obtain a 5% turbidity reduction.

A very preferred endochitinase is isolated from *Trichoderma harzianum* strain P1 having accession No. ATCC 74058. The protein has a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 as determined based on its elution profile from a chromatofocusing column, and a molecular weight of 40 kDa (as determined by sodium dodecyl sulfate polyacrylamide gel electrophoresis after the protein was prepared under reducing conditions, from a regression based on the log of molecular weight of standard proteins) and an isoelectric point of 3.9 as determined by isoelectric focusing electrophoresis from a regression of distance versus the isoelectric point of standard proteins. The specific activity of the purified endochitinase was determined to be 0.86 units/µg protein with the turbidity reducing assay and 2.2 nkatal /µg protein when nitrophenyl-β-D-N, N', N''-triacetylchitotriose was used as a substrate. The production and purification to homogeneity of this endochitinase are described in Harman et al U.S. Pat. No. 5,173,419, and also in Ser. No. 07/919,784, filed Jul. 27, 1992.

Another endochitinase is isolated from *Gliocladium virens* strain 41 having accession No. ATCC 20906 and has a molecular weight of 41 kDa ( as determined by sodium dodecyl sulfate polyacrylamide gel electrophoresis after the protein was prepared under reducing conditions, from a regression based on the log of molecular weight of standard proteins) and an isoelectric point of 7.8 as determined by isoelectric focusing from a regression of distance versus the isoelectric point of standard proteins. The procedures used for molecular weight determination and isoelectric point determination are the same as those described in detail in Ser. No. 07/919,784. The enzyme is active in citric acid/K$_3$(PO$_4$) buffer over a pH range of 3.5 to 7.0 and shows a 90–100% activity between pH 4.0 and 6.0 and shows maximum activity at pH 4.5. The optimum temperature for endochitinase activity at pH 5.5 is between 30° and 37° C., and activity drops off sharply at temperatures above 40° C. The production and purification to homogeneity of this enzyme are described in detail in Reference Example 1 hereinafter. The enzyme was purified to an activity 105-fold that of its activity in the culture filtrate.

The chitin 1,4-β-chitobiosidases cleave dimeric units from chitin from one end. Chitin 1,4-β-chitobiosidases are sometimes referred to for convenience hereinafter as chitobiosidases. Chitobiosidase activity is readily determined by measuring the release of p-nitrophenol from p-nitrophenyl-β-D-N,N'-diacetylchitobiose, e.g., by the following procedure. A substrate solution is formed by dissolving 3 mg of substrate in 10 ml 50 mM KHPO$_4$ buffer, pH 6.7. Fifty µl of substrate solution is added to a well in a microtiter plate (Corning). Thirty µl of test solution is added, and incubation is carried out at 50° C. for 15 minutes. Then the reaction is stopped by the addition of 50 µl of 0.4M Na$_2$CO$_3$, and the optical density is read at 410 nm. An activity of one nanokatal (nkatal) corresponds to the release of 1 nmol nitrophenol per second.

A chitobiosidase is isolated from *Trichoderma harzianum* strain P1 having accession No. ATCC 74058 and in its most prevalent form has a molecular weight of 36 kDa (as determined by sodium dodecyl sulfate polyacrylamide gel electrophoresis after the protein was prepared under reducing conditions, on direct comparison to migration of a 36 kDa protein), and an isoelectric point of 4.4±0.2 as determined based on its elution profile from a chromatofocusing column and a molecular weight of 40 kDa (as determined by sodium dodecyl sulfate polyacrylamide gel electrophoresis after the protein was prepared under reducing conditions, from a regression based on the log of the molecular weight of standard proteins), and an isoelectric point of 3.9 as determined by isoelectric focusing electrophoresis from a regression of distance versus isoelectric point of standard proteins. Conditions for molecular weight determination and isoelectric point determination are described in detail in Ser. No. 07/919,784. It has an optimum pH for activity of about 3 to 7. The production and purification of this chitobiosidase are described in Harman et al U.S. Pat. No. 5,173,419 where it is referred to as a chitobiase, and also in Ser. No. 07/919,784, filed Jul. 27, 1992, where it is referred to as a chitobiase and also as a chitobiosidase. The enzyme obtained in Ser. No. 07/919,784 has a specific activity of 127 nkatal/mg protein and is purified to greater than a 200-fold increase in specific activity compared to its activity in the culture filtrate. Ser. No. 07/919,784 refers to the presence also for a minor band at 36 kDa. It has since been discovered that the chitobiosidase from *Trichoderma harzianum* strain P1 (ATCC 74058) gives three closely spaced protein bands with molecular weights of 40 kDa (staining most intensely), 38 kDa (faintest stain) and 35 kDa (intermediate intensity stain), as determined by sodium dodecyl sulfate polyacrylamide gel electrophoresis after the protein was prepared under reducing conditions, from a regression based on the log of the molecular weight of standard proteins, and that the three bands represent different levels of N-glycosylation of the same protein. The term "biologically pure" as used herein includes the 40 kDa enzyme isolated as described above with or without the same protein with different level of glycosylation also being present.

The β-N-acetylglucosaminidases cleave monomeric units from chitin from one end. β-N-Acetylglucosaminidases may be referred to for convenience hereinafter as glucosaminidases. Glucosaminidase activity is readily determined by measuring the release of p-nitrophenol from p-nitrophenyl-β-D-N-acetylglucosaminide, e.g., by the same procedure as described above for assaying for chitobiosidase activity except for the substitution of substrate. An activity of one nanokatal (nkatal) corresponds to the release of 1 nmol nitrophenol per second. Glucosaminidase activity is present in culture filtrates from *Trichoderma harzianum* strain P1 having accession No. ATCC 74058 and from *Gliocladium virens* strain 41 having accession No. ATCC 20906.

The β-1,3-glucanolytic enzymes include, for example, glucan 1,3-β-glucosidases. The glucan 1,3-β-glucosidases cleave 1,3-β-glucans. The sources for these enzymes are typically the same as the sources for chitinolytic enzymes and are preferably microorganisms from the genera *Trichoderma* and *Gliocladium*. Glucan 1,3-β-glucosidase activity is readily determined by measuring the amount of reducing sugar release from laminatin in a standard assay containing 250 μl of enzyme solution and 250 μl of a 0.1% solution of laminarin in 50 mM potassium phosphate buffer, pH 6.7, wherein incubation is carried out at 30° C. for 1 hour whereupon 250 μl of a copper reagent (prepared by dissolving 28 g Na$_2$PO$_4$ and 40 g potassium sodium tatrate in 700 ml deionized water, adding 100 ml of 1N NaOH, then adding 80 ml of a 10% (w/v) solution of CuSO$_4$·5H$_2$O with stirring, then adding 180 g Na$_2$SO$_4$, when all the ingredients have dissolved, bringing to 1 L with deionized water, then allowing to stand for 2 days, then decanting and filtering) is added, and the admixture is covered with foil and heated for 20 minutes in a steam bath, whereupon, after cooling, 250 μl of arsenomolybdate reagent (prepared by dissolving 25 g of (NH$_4$)$_6$Mo$_7$O$_{24}$·4H$_2$O in 450 ml deionized water, adding 21 ml concentrated H$_2$SO$_4$ with mixing, then adding a solution containing 3 g Na$_2$HAsO$_4$·7H$_2$O in 25 ml distilled water and mixing, incubating at 37° C. for 2 days and storing in a brown bottle until used) is added with mixing, followed by adding of 5 ml deionized water, and reading color in a spectrophotometer at 510 nm, and wherein appropriate controls without either enzyme or substrate may be run simultaneously; the quantity of reducing sugar is calculated from glucose standards included in the assay. An activity of one nkatal corresponds to the release of 1 nmol glucose equivalent per second. Glucan 1,3-μ-glucosidase activity is present in culture filtrates from *Trichoderma harzianum* strain P1 having accession No. ATCC 74058 and from *Gliocladium virens* strain 41 having accession No. ATCC 20906.

A glucan 1,3-β-glucosidase is isolated from *Trichoderma harzianum* strain P1 having accession No. ATCC 74058 and has a molecular weight of 78 kDa (as determined by sodium dodecyl sulfate polyacrylamide gel electrophoresis after the protein was prepared under reducing conditions, from a regression based on the log of molecular weight of standard proteins) and an isoelectric point of 6.2 as determined by isoelectric focusing electrophoresis from a regression of distance versus the isoelectric point of standard proteins. The procedures for molecular weight determination and for isoelectric point determination are the same as those described in Ser. No. 07/919,784. The enzyme has activity against β-1,3 glucan laminarin between pH 4 and 7, with the strongest activity between 4.5 and 5.5. It releases glucose from laminarin at the same rate as reducing groups, which indicates that it is an exoglucanase cleaving monomeric glucose from the laminatin molecule. The enzyme is obtained and purified as generally described above with the medium for culturing of the microorganism being SMCS medium (the same medium used for production of endochitinase from *G. virens* as described in Reference Example 1 hereinafter). After the chromatofocusing step, several peaks with glucan 1,3-β-glucosidase activity are detected and fractions from major activity peaks are pooled, dialyzed, concentrated and applied to the Rotofor cell to obtain an electrophoretically pure exo-glucanase. The production and purification of the enzyme are described in detail in Reference Example 2 hereinafter. The enzyme was purified to a specific activity 35-fold that of its activity in the culture filtrate.

The cellulases are enzymes which cleave cellulosic polysaccharides. Cellulase activity is readily measured by the reducing group assay described previously except that cellulose or a cellulose derivative is substituted for laminatin. Other assays are known to those skilled in the art. One nkatal of activity corresponds to the release of 1 nmol glucose equivalent per second.

Cellulases are produced, for example, by fungi of the genera *Aspergillus*, (e.g., *Aspergillus niger*), *Trichoderma* (e.g., *Trichoderma viride*) and *Thielatia* (e.g., *Thielatia terrestris*).

We turn now to the non-enzymatic fungicides for use in the composition and method of the invention herein.

The sterol synthesis inhibiting fungicides include demethylation synthesis step inhibitors which are pyridines and pyrimidines and azoles including imidazoles and triazoles. Pyridines and pyrimidines are useful for agricultural purposes and include for example, triarimol, fenarimol, nuarimol, buthiobate and pyrifenox. Imidazoles useful for agricultural purposes include, for example, imazalil, prochloraz, and triflumidol. Imidazoles useful for medicinal purposes include, for example, miconazole, isoconazole, econazole, clotrimazole, bifonazole, butoconazole, ketoconazole, tioconazole, oxiconazole, fenticonazole, sulconazole and omoconazole. Triazoles useful for agricultural purposes include, for example, triadimefon, triadimenol, bitertanol, diclobutrazole, propiconazole, penconazole, diniconazole, flutriafol, flusilazole, hexaconazole, tebuconazole, myclobutanil, cyproconazole, furconazole and CGA 169374. Triazoles useful for medicinal purposes include, for example, vibunazole, terconazole, itraconazole, fluconazole and ICI 195-739.

The thiol group inactivating fungicides which are not specific to fungal cell membranes include, for example, captan which reacts with thiol compounds and thereby inactivates coenzyme A and other thiol compounds.

As previously indicated, the fungal cell wall degrading enzymes and non-enzymatic fungicides herein are present in the composition herein in a weight ratio of enzyme to non-enzymatic fungicide, i.e., of (a) to (b), on a biologically pure enzyme basis, ranging from 2:1 to 500,000:1. Preferably, the fungal cell wall degrading enzymes and non enzymatic fungicides herein are present in the composition herein in weight ratios of enzyme to non-enzymatic fungicide, i.e., of (a) to (b), on a biologically pure enzyme basis, as set forth in Table 1 below wherein "endochit" stands for endochitinase and "chitobios" stands for chitobiosidase.

TABLE 1

| Enzyme:fungicide combination | Preferred ratio |
| --- | --- |
| *T. harzianum* endochit:flusilazole | 10,000:1 to 85,000:1 |
| *T. harzianum* endochit:miconazole | 150:1 to 650:1 |
| *T. harzianum* endochit:captan | 25:1 to 450:1 |
| *T. harzianum* chitobios:flusilazole | 2,500:1 to 350,000:1 |
| *T. harzianum* chitobios:miconazole | 400:1 to 3,500:1 |
| *T. harzianum* chitobios:captan | 100:1 to 2,000:1 |
| *T. harzianum* glucosidase:flusilazole | 7,500:1 to 450,000:1 |
| *T. harzianum* glucosidase:miconazole | 75:1 to 45,000:1 |
| *T. harzianum* glucosidase:captan | 250:1 to 3,750:1 |
| *G. virens* endochit:flusilazole | 10,000:1 to 475,000:1 |
| *G. virens* endochit:miconazole | 250:1 to 4,000:1 |
| *G. virens* endochit:captan | 250:1 to 3,500:1 |

The compositions herein are readily formulated by admixing the fungal cell wall degrading enzymes and non-enzymatic fungicides with non-toxic carriers appropriate for the particular use for a composition, e.g., agriculturally acceptable carriers for agricultural uses and pharmaceutically acceptable carriers for medicinal uses. They may be formulated as liquids (solutions or suspensions) or as solids. To obtain the benefits of synergism, the concentration of the non-enzymatic fungicide should be below that in which it provides 95% or greater inhibition of spore germination when used alone. For liquid compositions, preferred concentrations have been found to be 1 to 500 ng/ml for flusilazole, 0.1 to 5 μg/ml for miconazole, and 0.1–2.5 μg/ml for captan for in vitro uses. Concentrations for practical agricultural uses and in vivo medicinal uses can differ according to application and delivery system and may range up to 10 times those listed above as preferred for in vitro uses.

We turn now to the method herein.

As previously indicated, the method herein is directed to inhibiting the replication, germination or growth of a fungus and comprises contacting such fungus or the locus to be protected from such fungus with an antifungal effective amount of appropriate composition herein.

More particularly, the method herein is directed to inhibiting the replication, germination or growth of a fungus and comprises contacting such fungus or the locus to be protected from such fungus with composition comprising (a) fungal cell wall degrading enzyme which preferably is biologically pure and (b) non-enzymatic fungicide selected from the group consisting of sterol synthesis inhibiting fungicides and thiol group inactivating fungicides in a weight ratio of (a) to (b) ranging from 2:1 to 500,000:1, on a biologically pure enzyme basis, the combination of (a) and (b) being present in an effective antifungal amount.

For medicinal purposes (i.e., human and veterinary therapy) the composition can be administered in the same way as the non-enzymatic fungicide is applied when used as the only active ingredient, e.g., topically applied to the skin of a human or non-human animal. Administration can also be, at least in some instances, via parenteral injection, e.g., intraperitoneally; this administration route is particularly useful where the immune system has been compromised since immune-deficient humans and individuals will inactivate enzymatic proteins more slowly than normal individuals.

For agricultural purposes, application can be, for example, to the seed, foliage, roots or fruit of a plant to be protected, or to the soil surrounding said plant, or to the fungus thereon which is to be inhibited. Normally, application is topical. However, other administration strategies can be used. For example, a gene coding for a fungal cell wall degrading enzyme can be isolated from microorganisms or other organisms producing it, and the gene inserted into the plant genome where it will produce the enzyme inside the plant, or transgenic endophytic microorganisms producing a fungal cell wall degrading enzyme can be used to infect plants internally, typically in the xylem, to produce enzyme internally in the plant, and said internally produced enzyme will act synergistically with non-enzymatic fungicide which has become systemic after topical application.

The method herein utilizes compositions herein containing fungal cell wall degrading enzymes, which are chitinolytic enzymes or $\beta$-1,3-glucanolytic enzymes, for application to fungi containing a structurally necessary amount of chitin and $\beta$-1,3-glucan, e.g., species from genera including *Fusarium, Gliocladium, Rhizoctonia, Trichoderma, Uncinula, Ustilago, Erysiphe, Botrytis, Saccharomyces, Sclerotium* and *Alternaria*. The specific examples hereinafter show synergism for the composition and method herein, in every instance where the non-enzymatic fungicide is used in a concentration less than that where it is substantially entirely effective alone, in application to *Botrytis cinerea*, a fungus which is pathogenic to fruits including grapes, raspberries, apples, and to beans and other crops, and which was selected in the work supporting this invention as a model test fungus.

The method herein utilizes compositions herein containing fungal cell wall degrading enzymes which are cellulases for application to lower fungi (i.e., Oomycetes) where the cell walls contain a structurally necessary amount of cellulosic polysaccharides, e.g., species from the genera *Pythium* and *Phytophtora*.

The synergistic interaction provided by the composition and method herein allows reduction of the quantity of non-enzymatic fungicide that is required for use for a particular inhibition of fungi as much 100- to 1000-fold and this reduction allows usage of fungicides which are otherwise too highly toxic or produce unacceptable side effects at fungicidal or fungistatic dosages, allows usage at dosages less than those which produce side effects and should reduce or at least delay the occurrence of natural resistance to important chemical fungicides.

An endochitinase isolated from *Gliocladium virens* strain 41 having accession No. ATCC 20906 is mentioned above. It can be prepared as described in Reference Example 1 below.

REFERENCE EXAMPLE 1

Synthetic medium was made up containing 680 mg $KH_2PO_4$, 870 mg $K_2HPO_4$, 200 mg KCl, 1 g $NH_4NO_3$, 200 mg $CaCl_2$, 200 mg $MgSO_4 \cdot 7H_2O$, 2 mg $FeSO_4$, 2 mg $ZnSO_4$, 2 mg $MnSO_4$, 42 g moist purified colloidal chitin (prepared as described in Vessey, J. C., et al, Trans. Br. Mycol. Soc. 60:710–713, 1973), 5 g sucrose, in 1 L distilled water, final pH 6.0.

100 ml of the synthetic medium was placed in a 250 ml Erlenmeyer flask.

The flask was inoculated with conidia grown by inoculation of potato dextrose agar (conidia of *Gliocladium virens* ATCC 20906) to provide $10^7$ conidia ml$^{-1}$ medium and the admixture was incubated at 25° C. for 5 or 7 days on a rotary shaker at 200 rpm. The culture filtrate was harvested by centrifugation at $8000 \times g$ for 10 minutes and removal of residual particulates by filtration through a glass fiber filter.

The purified endochitinase was isolated from the culture filtrate as described below with all steps being carried out at 4° C. except for concentration which was carried out at room temperature, The filtered culture filtrate was transferred into dialysis tubing (6,000 to 8,000 Da cutoff) and concentrated 30–40-fold by placing the tubing in solid polyethylene glycol (35,000 MW; Fluka Chemika-Biochemicha, Buchs, Switzerland). The concentrate was dialyzed overnight against 50 mM potassium phosphate buffer pH 6.7 (5 L buffer L$^{-1}$ culture filtrate) and applied to a gel filtration column ($5 \times 60$ cm) containing Sephacryl S-300 HR (Pharmacia LKB Biotechnology, Uppsala, Sweden) equilibrated with 50 mM potassium phosphate buffer pH 6.7 containing 200 mM NaCl. The material from 1 L of culture medium was chromatographed separately in two samples on Sephacryl S-300 HR. Fractions, approximately 8 ml each, were eluted with 1500 ml of 50 mM potassium phosphate buffer containing 200 mM NaCl. A first peak between fractions 70 and 120 contained high levels of chitobiosidase and N-acetyl-$\beta$-D-glucosaminidase activity. A second peak with endochitinase, $\beta$-1,3-glucanase, and chitobiosidase activity was detected in fractions 120 to 140. Fractions 140 to 160 contained endochitinase activity; proteins in this region were apparently not separated on the basis of molecular weight, but adsorbed to the gel matrix since they eluted at or greater than the total column volume. The fractions 140 to 160 from the first sample and similar fractions from the other, showing only endochitinase activity, were pooled. The pooled fractions (160ml ) were transferred into dialysis tubing (6,000 to 8,000 Da cut-off) and concentrated 30–40-fold by placing the tubing in solid polyethylene glycol (35,000 MW; Fluka Chemika-Biochemika, Buchs, Switzerland) and dialyzed overnight against a 20-fold volume of 25 mM ethanolamine-HCl buffer pH 8.7. The sample (about 25 ml) was then applied to a chromatofocusing column (1×30 cm) packed with PBE94 (Pharmacia LKB), and equilibrated with the same buffer used for dialysis. The column was eluted at a flow rate of 50 ml h$^{-1}$ with Polybuffer 96 (Pharmacia LKB) diluted 1:10 and adjusted to pH 7.0 with HCl according to the manufacturer's direction. A sharp peak at pH 8.0 containing endochitinase activity was detected in the eluted fractions. The peak fractions were pooled and the pooled fractions (about 40 ml) were dialyzed first against a 20-fold volume of 1M NaCl and then against a 40-fold volume of distilled water to remove Polybuffer, and concentrated to a volume of 2 ml in a collodion bag system (10,000 Daj UH 100/1, Schleicher & Schuell Inc., Keene, NH). The sample (2 ml ), i.e., the concentrated fractions, was applied to compartments 15 and 16 (pH 8.0–8.5) of a Rotofor isoelectric focusing cell (Bio-Rad, Richmond, Calif.) loaded with 35 ml distilled water containing 2% of Biolyte Ampholytes pH 3–10 (Bio-Rad), run at 12 W constant power, at a temperature of 40° C. after one hour of prefocusing run, and the run was continued for 5 hours. The fractions (each about 2 ml) were collected and assayed for endochitinase activity. The peak fractions contained homogeneous endochitinase as shown by the presence of a single protein band upon SDS-PAGE and upon Native PAGE. A single fluorescent activity band was observed following overlay of the native gel with the methylumbelliferyl substrate. This activity corresponded to the position of the single protein band detected with coomassie blue and silver stain.

The results of each purification step are summarized in Table 2 below. The endochitinase was purified 105-fold with a recovery of 8%. The quantity of endochitinase produced in the original culture filtrate was calculated to be at least 10 mg L$^{-1}$.

TABLE 2

| Step | Total protein (mg) | Enzyme activity (Units) | Specific activity (U mg$^{-1}$) | Purification (fold) | Yield (%) |
|---|---|---|---|---|---|
| Crude filtrate | 1065.0 | 10,400 | 9.7 | 1.0 | 100 |
| Dialysis | 192.0 | 9,066 | 47.2 | 4.8 | 87 |
| Sephacryl S-300 HR | 7.7 | 2,849 | 371.0 | 38.2 | 27 |
| Chromato- | 3.2 | 1,984 | 620.3 | 63.9 | 19 |

TABLE 2-continued

| Step | Total protein (mg) | Enzyme activity (Units) | Specific activity (U mg$^{-1}$) | Purification (fold) | Yield (%) |
|---|---|---|---|---|---|
| focusing Rotofor Cell | 0.8 | 815 | 1018.5 | 105.0 | 8 |

The peak (active) fractions were pooled, dialyzed against 1M NaCl and then against distilled water as described above, and concentrated to dryness in a Speedvac apparatus. The enzyme was stored at −20° C. and reconstituted in an appropriate volume of sterilized distilled water for use.

A glucan 1,3-$\beta$-glucosidase isolated from *Trichoderma harzianum* strain P1 having accession No. ATCC 74058 is mentioned above. It can be prepared as described in detail in Reference Example 2 below.

REFERENCE EXAMPLE 2

Crude enzyme solutions were prepared using the growth conditions described for Reference Example 1, except that strain P1 of *T. harzianum* was substituted for *G. virens* ATCC 20906.

All procedures except concentration steps were carried out at 4° C. Enzyme solutions were concentrated at room temperature. The filtered culture filtrate was transferred into dialysis tubing (6,000 to 8,000 Da cutoff) and concentrated 20-fold by placing the tubing in solid polyethylene glycol (35,000 MW; Fluka Chemika-Biochemika, Buchs, Switzerland). The concentrate was dialyzed overnight against 50 mM potassium phosphate buffer pH 6.7 (5 L buffer L$^{-1}$ culture filtrate) and applied to a gel filtration column (5×60 cm) containing Sephacryl S-300 HR (Pharmacia LKB Biotechnology, Uppsala, Sweden) equilibrated with 50 mM potassium phosphate buffer pH 6.7 containing 200 mM NaCl. Fractions (10 ml) were eluted with the same buffer using reverse flow at a rate of 140 ml h$^{-1}$. The material from 1 liter of culture medium was chromatographed separately in two samples on Sephacryl S-300 HR, and fractions (numbers 72 to 84 from the first sample, similar ones from the second) containing glucosidase activity were pooled (approximately 230 ml) and concentrated to about 20 ml as described above. They were then dialyzed overnight against a 20-fold volume of 25 mM Tris-CH$_3$COOH buffer, pH 8.0. The sample was then applied to a chromatofocusing column (1×30 cm) packed with PBE 94 (Pharmacia LKB), and equilibrated with the same buffer used for dialysis. The column was eluted at a flow rate of 50 ml h$^{-1}$ with Polybuffer 96 (Pharmacia LKB), diluted 1:13 and adjusted to pH 7.0 with CH$_3$COOH according to the manufacturer's directions. Fractions of interest (fractions 13 to 16; 24 ml total) were pooled, dialyzed first against a 20-fold volume of 1 M NaCl and then against a 40-fold volume distilled water to remove Polybuffer, and concentrated to a volume of 2 ml in a collodion bag system (10,000 Da cutoff; UH 100/1, Schleicher & Schuell Inc., Keene, NH). The enzyme solution was stored at −20 C. until use.

The results of the purification from 1 L culture filtrate are summarized in Table 3 below.

TABLE 3

| Step | Total protein (mg) | Enzyme activity (nkatal) | Specific activity (nkatal mg$^{-1}$) | Purification (fold) | Yield (%) |
|---|---|---|---|---|---|
| Dialyzed culture filtrate | 450 | 1938 | 4.3 | 1.0 | 100 |
| Sephacryl S-300 HR | 144 | 907 | 6.3 | 1.5 | 47 |
| Chromatofocusing | 2.3 | 351 | 153 | 36 | 18 |

The invention is illustrated by the specific examples set forth below.

EXAMPLE I

The non-enzymatic fungicides tested were flusilazole (E.I. dupont de Nemours), miconazole (Sigma Chemical Co.), and captan (liquid formulation containing 37% captan as the only active ingredient, Gustafson, Plano, Tex.). For the assays herein, the flusilazole was dissolved in acetone, the miconazole was dissolved in 50% ethanol, and the captan was suspended in deionized water.

The enzymes tested were endochitinase from *Trichoderma harzianum* strain P1 (ATCC 74058) prepared as described in Harman et al U.S. Pat. No. 5,173,419 and also in Ser. No. 07/919,784, filed Jul. 27, 1992; the endochitinase from *Gliocladium virens* strain 41 (ATCC 20906) prepared as described in Reference Example 1; the 40 kDa chitobiosidase from *Trichoderma harzianum* strain P1 (ATCC 74058) prepared as described in Harman et al in Ser. No. 07/919,784, filed Jul. 27, 1992; and the glucan 1,3-β-glucosidase from *Trichoderma harzianum* strain P1 (ATCC 74058) prepared as described in Reference Example 2. The enzymes tested were dissolved in deionized water.

Assay mixtures were prepared that contained 20 μl of a conidial suspension ($10^5$ to $10^6$ conidia/ml) of the test fungus, which was the plant pathogen *Botrytis cinerea*, 20 μl of a nutrient solution, potato dextrose broth (Difco Laboratories, Detroit, Mich.) made at 3 times the standard rate, 18 μl of an enzyme solution made to the appropriate concentration (for controls, water was substituted), and 2μl of the solution or suspension of the non-enzymatic fungicide. As controls, the various solvent solutions were tested at the final concentrations employed, but they had no effect on the test fungus.

Mixtures as indicated above were placed in sterile Eppendorf tubes and incubated 24 to 30 hours at 25° C. Portions of the mixtures were placed on a microscope slide and the germination of the first 100 conidia seen were evaluated. Each treatment was done in triplicate in each experiment, and each experiment was repeated. Percent inhibition was calculated according to the following equation: %I=(1-%S$_t$/%S$_c$)×100, where %I represents the percentage inhibition, %S$_t$ represents percentage germination of spores in the treatment of interest, and %S$_c$ represents the percentage of spores germinating in the control (i.e., with neither non-enzymatic fungicide, nor enzyme). Appropriate concentrations of the various enzymes and non-enzymatic fungicides were evaluated by preliminary experiments which determined the dosage response curve for each substance singly. Concentrations of enzyme solutions were employed ranging from 0 to 100 μg/ml, and the concentration of non-enzymatic fungicide was chosen that provided about 20% inhibition of spore germination of *B. cinerea*. The concentration for each chemical is provided in the tables below. Results for combinations of non-enzymatic fungicide and endochitinase from *Trichoderma harzianum* strain P1 are set forth in Table 4 below.

TABLE 4

| Fungicides | % inhibition of different concentrations of enzyme (μg ml$^{-1}$) | | | | |
|---|---|---|---|---|---|
| | 0 | 25 | 50 | 75 | 100 |
| Captan (0.5 μg ml$^{-1}$) | 23 | 72 | 97 | 100 | 100 |
| Flusilazole (5 ng ml$^{-1}$) | 18 | 99 | 100 | 100 | 100 |
| Miconazole (0.5 μg ml$^{-1}$) | 19 | 100 | 100 | 100 | 100 |
| None | 0 | 29 | 61 | 65 | 73 |

Results for combinations of non-enzymatic fungicide and endochitinase from *Gliocladium virens* strain 41 (ATCC 20906) are set forth in Table 5 below.

TABLE 5

| Fungicides | % inhibition of different concentrations of enzyme (μg ml$^{-1}$) | | | | |
|---|---|---|---|---|---|
| | 0 | 25 | 50 | 75 | 100 |
| Captan (0.5 μg ml$^{-1}$) | 23 | 65 | 80 | 98 | 100 |
| Flusilazole (5 ng ml$^{-1}$) | 18 | 89 | 100 | 100 | 100 |
| Miconazole (0.5 μg ml$^{-1}$) | 19 | 99 | 100 | 100 | 100 |
| None | 0 | 0 | 0 | 24 | 35 |

Results for combinations of non-enzymatic fungicide and chitobiosidase from *Trichoderma harzianum* strain P1 (ATCC 74058) are set forth in Table 6 below.

TABLE 6

| Fungicides | % inhibition of different concentrations of enzyme (μg ml$^{-1}$) | | | | |
|---|---|---|---|---|---|
| | 0 | 25 | 50 | 75 | 100 |
| Captan (0.5 μg ml$^{-1}$) | 23 | 55 | 78 | 98 | 100 |
| Flusilazole (5 ng ml$^{-1}$) | 18 | 60 | 100 | 100 | 100 |
| Miconazole (0.5 μg ml$^{-1}$) | 19 | 85 | 100 | 100 | 100 |
| None | 0 | 11 | 20 | 24 | 28 |

Results for combinations of non-enzymatic fungicide glucan 1,3-β-glucosidase from *Trichoderma harzianum* strain P1 (ATCC 74058) are set forth in Table 7 below.

TABLE 7

| Fungicides | % inhibition of different concentrations of enzyme (μg ml$^{-1}$) | | | | |
|---|---|---|---|---|---|
| | 0 | 25 | 50 | 75 | 100 |
| Captan (0.5 μg ml$^{-1}$) | 23 | 67 | 77 | 93 | 100 |
| Flusilazole (5 ng ml$^{-1}$) | 18 | 49 | 63 | 89 | 100 |
| Miconazole (0.5 μg ml$^{-1}$) | 19 | 50 | 70 | 88 | 100 |
| None | 0 | 17 | 32 | 40 | 50 |

Every fungicide/enzyme combination provided a synergistic interaction. The most appropriate equation to test for synergy was described by Richer (Richer, D. L. Pestic. Sci. 19, 309–315, 1987) as Limpel's formula $E_e = X + Y - XY/100$, where $E_e$ is the expected effect from additive responses of the chemicals and X and Y are percentage inhibition of the chemicals. Thus, if X provides 20% inhibition and Y provides 30%, the expected additive effect is 20+30−(20×30)/100=44%. Any value greater than 44% is evidence of synergy. This equation is based on the consideration that if X kills 20% of the organisms available, then only 80% of the total are available to Y.

The tables above provide values for each non-enzymatic fungicide/enzyme combination, with the non-enzymatic fungicide used at the $ED_{20}$ level (dose effective to cause 20% inhibition when non-enzymatic fungicide is used alone) and enzyme concentrations ranging from 0 to 100 μg/ml. The levels of synergy shown are substantial; for example, miconazole alone at 0.5 μg/ml gave 19% inhibition and the endochitinase from *G. virens* alone at 25 μg/ml gave 0% inhibition, while the combination gave 99% inhibition.

EXAMPLE II

The assay procedure, enzymes, and non-enzymatic fungicides were the same as those used in Example I. As in Example I, the test fungus was *B. cinerea*.

Figure 2:
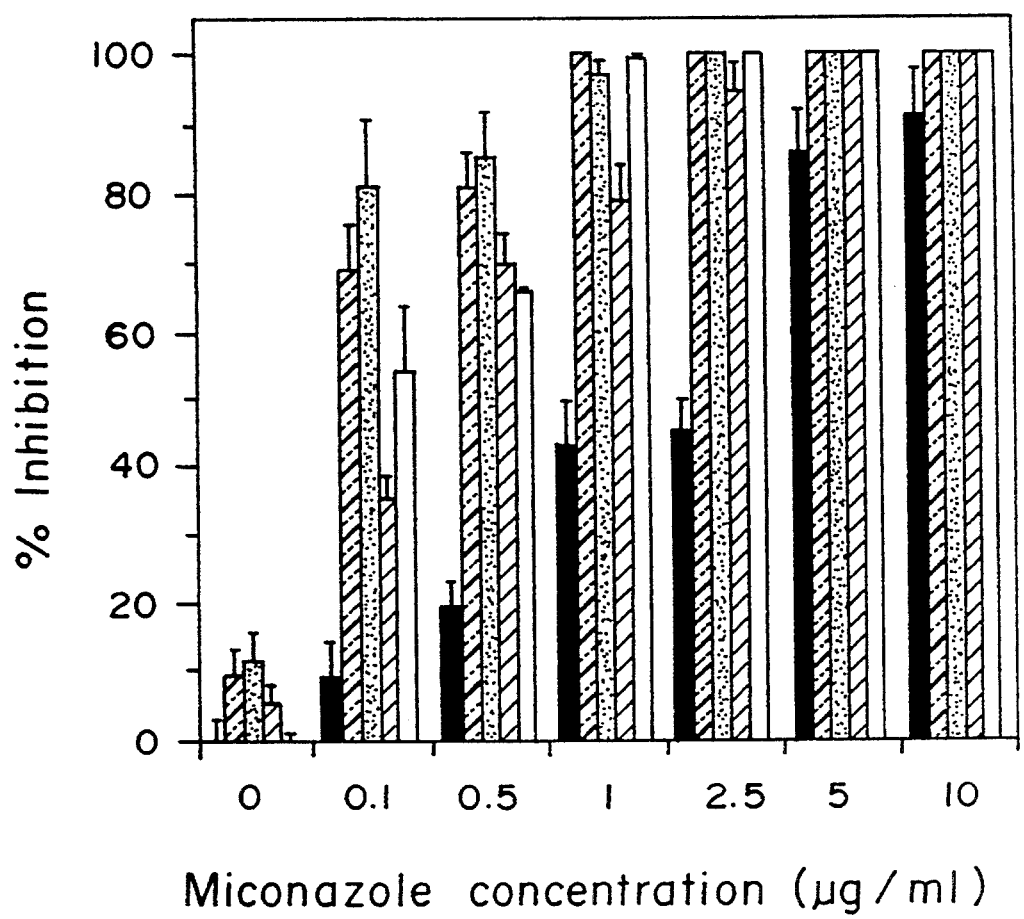
FIG. 2 is a set of bar graphs depicting % inhibition at various miconazole concentrations, in the presence of different enzymes and in the absence of enzyme, showing results of Example II.
Figure 3:
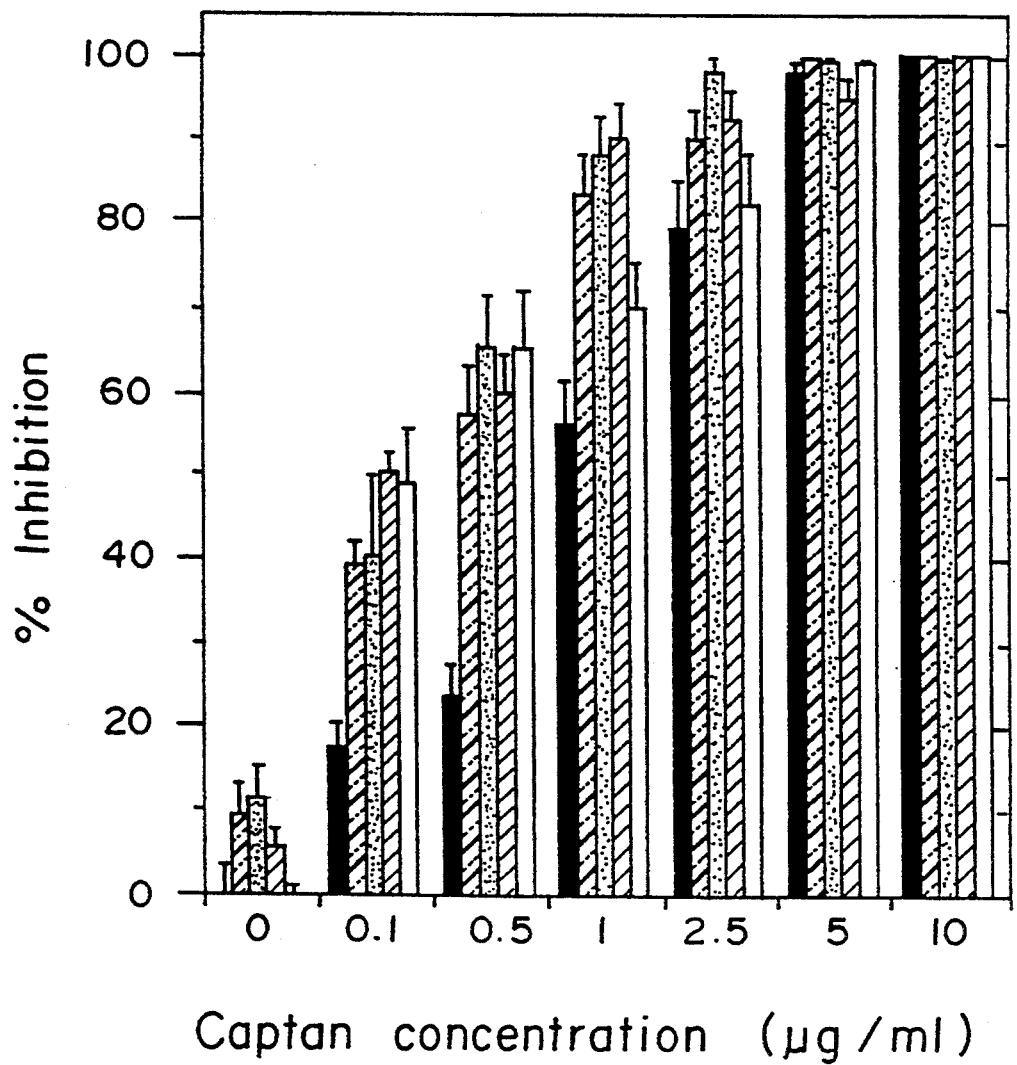
FIG. 3 is a set of bar graphs depicting % inhibition at various captan concentrations, in the presence of different enzymes and in the absence of enzyme, showing results of Example II.

Results are presented in FIGS. 1–3 which are bar graphs showing % inhibition at non-enzymatic fungicide concentrations as recited, in the presence of enzyme and in the absence of enzyme, wherein the totally black bars denote no enzyme, the hatched bars with alternating black and dotted lines denote endochitinase from *Trichoderma harzianum* strain P1 (ATCC 74058) at 10 μg/ml, the bars filled in with dots denote 40 kDa chitobiosidase from *Trichoderma harzianum* strain P1 (ATCC 74058), the bars hatched with alternating open areas and lines denote glucan 1,3-β-glucosidase from *Trichoderma harzianum* strain P1 (ATCC 74058) and the bars that are open denote endochitinase from *Gliocladium virens* strain 41 (ATCC 20906). In the graphs, error bars indicate standard deviations. The values for inhibition are means across two experiments with three replicates for each experiment.

Results are also set forth in Table 8 below wherein $E_e$ is the expected effect from an additive response according to Limpel's formula expressed as percent inhibition and $I_o$ is the percent inhibition observed and "Endoc. (P1)" stands for endochitinase from *Trichoderma harzianum* strain P1 (ATCC 74058), "Chitob. (P1)" stands for chitobiosidase from *Trichoderma harzianum* strain P1 (ATCC 74058), "Glucan.(P1)" stands for glucan 1,3-β-glucosidase from *Trichoderma harzianum* strain P1 (ATCC 74058) and "Endoc.(41)" stands for endochitinase from *Gliocladium virens* strain 41 (ATCC 20906), and each of the enzymes was used at a concentration of 25 μg/ml.

TABLE 8

| Toxins (concentration) | Endoc. (P1) 25 μg ml$^{-1}$ | | Chitob. (P1) 25 μg ml$^{-1}$ | | Glucan. (P1) 25 μg ml$^{-1}$ | | Endoc. (41) 25 μg ml$^{-1}$ | |
|---|---|---|---|---|---|---|---|---|
| | $E_e$ | $I_o$ | $E_e$ | $I_o$ | $E_e$ | $I_o$ | $E_e$ | $I_o$ |
| Flusilazole (5 ng ml$^{-1}$) | 41 | 99 | 27 | 60 | 22.1 | 65 | 18 | 67 |
| Miconazole (0.5 μg ml$^{-1}$) | 42.5 | 100 | 27.9 | 85 | 23 | 70 | 19 | 66 |
| Captan (0.5 μg ml$^{-1}$) | 46.7 | 85 | 33.2 | 55 | 28.7 | 60 | 25 | 63 |

Table 9 below shows ED50 values for endochitinase from *Trichoderma harzianum* strain P1 (ATCC 74058) and for the non-enzymatic fungicides tested with no endochitinase and with endochitinase at concentrations indicated. $ED_{50}$ is the dose effective for 50% inhibition.

TABLE 9

| | Endochitinase (ED$_{50}$ of 41 μg ml$^{-1}$) (μg ml$^{-1}$) | | |
|---|---|---|---|
| Fungicides | 0 | 10 | 25 |
| Flusilazole | 0.06 | 0.0007 | 0.0003 |
| Miconazole | 3.0 | 0.06 | 0.04 |

TABLE 9-continued

| | Endochitinase (ED$_{50}$ of 41 μg ml$^{-1}$) (μg ml$^{-1}$) | | |
|---|---|---|---|
| Fungicides | 0 | 10 | 25 |
| Captan | 0.9 | 0.3 | 0.06 |

Table 10 below shows ED50 values for chitobiosidase from *Trichoderma harzianum* strain P1 (ATCC 74058) and for the non-enzymatic fungicides tested with no chitobiosidase and with chitobiosidase at concentrations indicated.

TABLE 10

| | Chitobiosidase (ED$_{50}$ of 152 μg ml$^{-1}$) (μg ml$^{-1}$) | | | | |
|---|---|---|---|---|---|
| Fungicides | 0 | 25 | 50 | 75 | 100 |
| Flusilazole | 0.06 | 0.001 | 0.0004 | 0.00035 | 0.0003 |
| Miconazole | 3.0 | 0.06 | 0.045 | 0.04 | 0.03 |
| Captan | 0.9 | 0.25 | 0.175 | 0,08 | 0.05 |

Table 11 below shows ED50 values for glucan 1,3-β-glucosidase from *Trichoderma harzianum* strain P1 (ATCC 74058) and for the non-enzymatic fungicides tested with no glucosidase and with glucosidase at concentrations indicated.

TABLE 11

| | Glucosidase (ED$_{50}$ of 90 μg ml$^{-1}$) (μg ml$^{-1}$) | | | |
|---|---|---|---|---|
| Fungicides | 0 | 25 | 50 | 75 |
| Flusilazole | 0.06 | 0.0033 | 0.001 | 0.00017 |
| Miconazole | 3.0 | 0.27 | 0.04 | 0.0018 |
| Captan | 0.9 | 0.1 | 0.08 | 0.02 |

Table 12 below shows ED50 values for endochitinase from *Gliocladium virens* strain 41 (ATCC 20906) and for the non-enzymatic fungicides tested with no endochitinase and with endochitinase at concentrations indicated.

TABLE 12

| | Endochitinase (ED$_{50}$ of 195 μg ml$^{-1}$) (μg ml$^{-1}$) | | | | |
|---|---|---|---|---|---|
| Fungicides | 0 | 25 | 50 | 75 | 100 |
| Flusilazole | 0.06 | 0.0025 | 0.001 | 0.0045 | 0.00022 |
| Miconazole | 3.0 | 0.092 | 0.06 | 0.04 | 0.025 |
| Captan | 0.9 | 0.1 | 0.085 | 0.042 | 0.030 |

In data not depicted in figures or shown in tables, the addition of 1 ng ml$^{-1}$ of flusilazole reduced the $ED_{50}$ value 6.8-fold for endochitinase from *Trichoderma harzianum* strain P1 (ATCC 74058) and 4.6-, 1.3- and 3.9-fold for chitobiosidase and glucanase from *Trichoderma harzianum* strain P1 (ATCC 74058) and endochitinase from *Gliocladium virens* strain 41 (ATCC 20906), respectively.

The addition of the cell wall degrading enzymes to the preparations of non-enzymatic fungicides at the concentrations tested increased the occurrence of morphological changes such as lysis of the mycelium and hyphal tips in the germinating spores of *B. cinerea*.

Results of the examples show the reduction of the quantity of the non-enzymatic fungicides necessary to obtain any level of inhibition when such fungicides were used in combination with the enzymes tested.

Variations in the invention will be obvious to those skilled in the art. Therefore, the invention is defined by the claims.

What is claimed is:

1. A composition for inhibiting the germination or growth of a fungus, said composition comprising
   (a) a fungal cell wall degrading enzyme, selected from the group consisting of endochitinases, chitin 1,4-β-chitobiosidases, β-N-acetylglucosaminidases, and glucan 1,3-β-glucosidases,
   (b) a non-enzymatic fungicide selected from the group consisting of (i) sterol synthesis inhibiting fungicides and (ii) captan, said non-enzymatic fungicide being present at a concentration providing about 4% to less than 95% inhibition of spore germination when used without (a),
   (a) and (b) being present in a weight ratio of (a) to (b) ranging from 2:1 to 500,000:1.

2. The composition of claim 1 wherein the fungal cell wall degrading enzyme is selected from the group consisting of endochitinases, chitin 1,4-β-chitobiosidases, and glucan 1,3-β-glucosidases.

3. The composition of claim 2 wherein the fungal cell wall degrading enzyme is an endochitinase.

4. The composition of claim 3 wherein the endochitinase is isolated from *Trichoderma harzianum* strain P1 having accession No. ATCC 74058.

5. The composition of claim 4 wherein the non-enzymatic fungicide is a sterol synthesis inhibiting fungicide.

6. The composition of claim 5 wherein the sterol synthesis inhibiting fungicide is an azole.

7. The composition of claim 6 wherein the azole is flusilazole, and the weight ratio of (a) to (b) ranges from 10,000:1 to 85,000:1.

8. The composition of claim 6 wherein the azole is miconazole, and the weight ratio of (a) to (b) ranges from 150:1 to 650:1.

9. The composition of claim 1 wherein the non-enzymatic fungicide is captan, and the weight ratio of (a) to (b) ranges from 25:1 to 450:1.

10. The composition of claim 1 where (a) and (b) are present in a weight ratio which provides synergistic interaction between (a) and (b) in inhibiting the germination or growth of a fungus.

11. A method of inhibiting the germination or growth of a fungus, which comprises contacting said fungus or the locus to be protected from said fungus with an amount of the composition of claim 1 effective to obtain said inhibiting.

12. A method of inhibiting the germination or growth of a chitin- and 1,3-β-glucan-containing fungus, which comprises contacting said fungus or the locus to be protected from said fungus, with an amount of the composition of claim 2 effective to obtain said inhibiting.

13. The method of claim 12 wherein said fungus is of the genus *Botrytis*.

14. The method of claim 13 wherein the fungus is *Botrytis cinerea*.

* * * * *